United States Patent
Buhring et al.

(10) Patent No.: US 6,949,346 B2
(45) Date of Patent: *Sep. 27, 2005

(54) METHOD FOR BINDING BASOPHILS AND MAST CELLS

(75) Inventors: Hans-Jorg Buhring, Tubingen (DE); Johannes Andreas Van Agthoven, Marseilles (FR); David Jarossay, CH-Bellinzona (CH)

(73) Assignee: Eberhard-Karls-Universität Tübingen Universitaäsklinikum, Tübingen (DE)

( * ) Notice: Subject to any disclaimer, the term of this patent is extended or adjusted under 35 U.S.C. 154(b) by 45 days.

This patent is subject to a terminal disclaimer.

(21) Appl. No.: 09/996,030

(22) Filed: Nov. 16, 2001

(65) Prior Publication Data

US 2002/0160429 A1 Oct. 31, 2002

Related U.S. Application Data

(63) Continuation of application No. PCT/EP00/04468, filed on May 17, 2000.

(30) Foreign Application Priority Data

May 19, 1999 (DE) .......................................... 199 22 863
Jun. 12, 1999 (DE) .......................................... 199 26 879

(51) Int. Cl.[7] ....................... G01N 33/53; A61K 39/395
(52) U.S. Cl. ....................... 435/7.1; 435/7.21; 436/501; 530/387.1; 424/130.1; 424/141.1
(58) Field of Search ................................ 435/7.1, 7.21; 436/501; 530/387.1; 424/130.1, 141.112, 120.1

(56) References Cited

U.S. PATENT DOCUMENTS

| | | | | |
|---|---|---|---|---|
| 6,306,575 B1 | 10/2001 | Thomas | ......................... | 435/2 |
| 6,323,321 B1 | 11/2001 | Bühring | .................... | 530/387.2 |

FOREIGN PATENT DOCUMENTS

| | | | | |
|---|---|---|---|---|
| DE | 19632755 | 1/1998 | .......... | C07K/16/30 |
| DE | 199 18 446.1 | 12/2001 | | |
| EP | 0 598 479 A2 | 5/1994 | | |
| EP | 0863157 | 12/1997 | .......... | C07K/16/28 |
| WO | WO 98/32014 | 1/1997 | .......... | G01N/33/50 |
| WO | WO 97/46880 | 6/1997 | .......... | G01N/33/543 |

OTHER PUBLICATIONS

Blom et al., "Phenotypic characterization of KU812 A cell line identified as an immature human basophilic leukocyte." European Journal of Immunology, 1992, vol. 22, No. 8, pp. 2025–2032. Abstract Only.*

Hermine et al. Granulocyte–macrophage colony–stimulating factor and erythropoietin act competitively to induce two different programs of differentiation in the human pluripotent cell line UT–7. Blood, 1992, vol. 80, No. 12, pp. 3060–3069. Abstract Only.*

Dec. 9, 2003 Office Action issued in related Japanese Patent Application No. 2000–620348.

Ashman, et al. "Expression of the YB5.B8 Antigen (c–kit proto–oncogene product) in Normal Human Bone Marrow)." *Blood*. vol. 78, No. 1, pp. 30–37, Jul., 1991.

Bodger, et al. "A Monoclonal Antibody Reacting with Human Basophils." *Blood*, vol. 69, No. 5, pp. 1414–1418, May, 1987.

Colby, et al., "*Germacrene C Synthase from Lycopersicon Esculentum cv. VFNT Cherry Tomato: cDNA Isolation, Characterization, and Bacterial Expression of the Multiple Product Sesquiterpene Cyclase*," Proc. Natl. Acad. Sci., vol. 95, pp. 2216–2221, dated Mar. 1998.

Kroes, et al. "*Bacterial Diversity within the Human Subgingival Crevice*," PNAS, vol. 96, No. 25, pp. 14547–14552, dated Dec. 7, 1999.

De Kraker, et al., "(+)–Germacrene A Biosynthesis: *The Committed Step in the Biosynthesis of Bitter Sesquiterpene Lactones in Chicory*," Plant Physiol., vol. 117, pp. 1381–1392 (1998).

* cited by examiner

*Primary Examiner*—Long V. Le
*Assistant Examiner*—Lisa V. Cook
(74) *Attorney, Agent, or Firm*—Knobbe, Martens, Olson & Bear, LLP (57) ABSTRACT

The present invention relates to an antibody for the detection quantification, or isolation of basophils, mast cells, the precursor cells of basophils or mast cells, or a surface structure of basophils or mast cells. This antibody corresponds to an antibody with the designation 97A6, produced and released by hybridoma cells that were deposited in accordance with the Budapest Treaty on Feb. 12, 1997 under accession number DSM ACC 2297 at Deutsche Sammlung von Mikroorganismen und Zellkulturen GmbH (DSMZ).

9 Claims, 4 Drawing Sheets

METHOD FOR BINDING BASOPHILS AND
MAST CELLS

RELATED APPLICATION

This is a continuation of International Patent Application PCT/EP00/04468, filed May 17, 2000 and published in German, which claims priority to German application number 19922863.9, filed May 19, 1999, and German application number 19926879.7, filed Jun. 12, 1999. The German applications are incorporated herein by reference.

BACKGROUND OF THE INVENTION

1. Field of the Invention

The present invention relates to the use of an antibody for the detection and/or quantification and/or isolation of basophils and/or mast cells and/or of the precursor cells of basophils and/or mast cells and/or of a surface structure of said cells.

The invention further concerns a method for studying allergies;

a method for providing hematopoietic precursor cells that can differentiate into mast cells or basophils;

a substantially pure population of basophils and/or mast cells and/or of the precursor cells of basophils and/or mast cells; as well as a reagent for binding said cells.

2. Related Prior Art

Antibodies with which basophils and mast cells, in the mature state thereof, can each be detected, each individually, are known.

In hematopoiesis, also called blood formation, lymphoid and myeloid precursor cells arise from pluripotent stem cells in bone marrow. The lymphoid precursor cells give rise to T- and B-lymphocytes, while the myeloid precursor cells give rise to either erythrocytes, megakaryocytes, basophils, eosinophils, neutrophils, monocytes, or as-yet unknown precursor cells from which mast cells develop. Basophils, eosinophils, and neutrophils are together referred to as granulocytes. After hematopoiesis, basophils are present in the blood, while mast cells are present in tissues. In adults, hematopoiesis takes place in bone marrow.

Basophils and mast cells are multifunctional effector cells which participate in allergic and inflammatory reactions. Despite their similar biochemical and functional properties, basophils and mast cells are different cell types which both—like eosinophils—derive from CD34-positive precursor cells.

Distinguishing among the various cell types in the bone marrow and blood, and assigning them to various stages of differentiation, is an essential part of everyday clinical practice. For example, in order to diagnose blood-formation disorders it is necessary to determine the number of cells of each specific cell type, and if possible also their respective stages of differentiation.

In addition, the analysis of blood cells and blood precursor cells in the bone marrow is important in the diagnosis of leukemias. The number, type and stage of the cells are utilized to classify or allocate the type of leukemia, and to decide as to an appropriate therapy. Allocation of leukemia is based on the one hand on the clinical course of the disease, and on the other hand on the degree of maturation and the lineage of the pathologically altered leukocytes. This requires, however, determination of the cell type and status of both the healthy and the degenerate cells contained in a sample from a patient.

Up to now, these analyses are being performed under the microscope based on the morphology of the cells, after staining with conventional staining methods, for example Pappenheim staining or May-Grünwald-Giemsa staining, and by manual counting. Modern methods for the evaluation of bone marrow biopsies or blood samples use antibodies that recognize specific antigens as markers for certain cell types and stages. The antibodies and the recognized antigens, respectively, can then be automatically detected using standard methods such as ELISA (enzyme-linked immunosorbent assay) or flow cytometry (FACS: fluorescence-activated cell sorting).

Only a few antibodies which specifically recognize intact basophils are presently known, however. One of these antibodies is the antibody Bsp-1, which reacts with basophils but not with tissue mast cells (Bodger, M. P. et al., Blood 69 (1987), 1414). The CD117-reactive antibody YB5B8 recognizes mast cells and hematopoietic precursor cells (Ashman et al., Blood 78 (1991), 30).

DE 197 08 877 C1 describes the fact that antibody 97A6 binds specifically to megakaryocytes but not to thrombocytes.

No antibody is hitherto known, however, to simultaneously recognize basophils, mast cells, as well as their precursor cells.

SUMMARY OF THE INVENTION

In view of the above, it is an object of the present invention to provide an antibody for the use mentioned at the outset.

According to the present invention, this object is achieved by a use of an antibody in which binding of the antibody occurs to that surface structure of the cells to which can bind the antibody with the designation 97A6, produced and released by hybridoma cells that were deposited in accordance with the Budapest Treaty on Feb. 12, 1997 under number DSM ACC 2297 at Deutsche Sammlung von Mikroorganismen und Zellkulturen GmbH, DMSZ. All restrictions upon public access to the deposit will be irrevocably removed upon the grant of a patent on this Application and the deposit will be replaced if viable samples cannot be dispensed by the depository.

The storage term of these hybridoma cells has been correspondingly extended.

Also understood as an antibody within the meaning of the invention are antibody fragments, for example F(ab), conjugates with antibodies and/or antibody fragments, and all compositions which contain antibodies, antibody fragments, and conjugates with antibodies and/or antibody fragments.

A surface structure to which an antibody binds can be, within the meaning of the invention, an individual molecule, for example a membrane protein, or also an association of two or more molecules, for example an ion channel or receptor comprising several subunits.

The object underlying the invention is completely achieved in this fashion.

Specifically, the inventors of the present Application have recognized that the surface structure to which antibody 97A6 can bind is expressed, with the exception of a few megakaryocytic cell lines, only on basophils and mast cells and on their precursor cells, and on mast cell line HMC-1 and basophilic leukemia cell line KU-812. This was not to be expected based on DE 197 08 877 C1, since the latter describes the fact that antibody 97A6 is specific for megakaryocytes.

Recent results of research by the inventor indicate, however, that antibody 97A6 recognizes a few megakaryocytic cell lines, but no native megakaryocytes.

Since the antibody used according to the present invention is well-suited for the purification of cells, the invention also concerns a substantially pure population of basophils and/or mast cells and/or of precursor cells of basophils and/or mast cells, said cells being capable of binding a reagent that specifically binds to those surface structures of said cells that are recognized by antibody 97A6. The invention moreover concerns a corresponding reagent for binding said cells.

Using antibody 97A6, it is readily possible to isolate the surface structure to which the antibody binds, and to produce both monoclonal and polyclonal antibodies against it.

Via FACS analysis it could be shown by now, that the surface structure represents the phosphodiesterase/nucleotide pyrophosphatase ectoenzyme PDNP3, which is also referred to as NPP3 or PD-Ibeta. The sequence was published by Jin-Hua et al. in Genomics 45, 421–415 (1997).

One great advantage of the use according to the present invention of an antibody lies in the fact that it is thereby reliably possible to monitor the number of basophils in the blood of patients with chronic myeloid leukemia (CML), since many of the basophils present in immature form, which hitherto were not morphologically identifiable as such, can be reliably recognized thereby. The exact number of basophils in such patients, and thus the status of their disease, can thus be ascertained.

The use according to the present invention of an antibody furthermore advantageously makes possible the isolation of precursor cells from which, depending on the cultivation conditions, mast cells or basophils can be generated. The use according to the present invention thus facilitates analysis of the differentiation of such cells. It is particularly advantageous in this context that with the antibody that is used, as compared with other antibodies hitherto known, basophils are detectable at very early development stages, and remain detectable with the antibody as they develop further.

An important advantage of the use according to the invention of an antibody in terms of routine diagnostics is the capability of detecting with a single antibody, for example, mast cells from various tissues and basophils from blood. Different antibodies and antibody combinations were hitherto necessary for this purpose, involving considerable extra cost. Basophils in blood samples can also be histochemically stained, for example using May-Grünwald-Giemsa. Experienced personnel are then needed to identify and count the basophils, and subjective fluctuations in the results are possible. Immature basophils cannot be identified in this manner. The use according to the present invention of antibodies, on the other hand, makes possible analysis using objectively analyzable standard methods, such as ELISA or FACS, which can be performed even by less-experienced personnel and allow a much greater sample throughput than the subjective evaluation of stains.

The inventors of the present Application have moreover recognized that the activation of basophils, for example in conjunction with an allergic reaction, results in an enhanced presentation of the surface structure recognized by the antibody that is used according to the present invention. The detection and/or quantification of this surface structure on basophils is therefore well suited for studying the activation of basophils.

In a preferred embodiment, the antibody used is a monoclonal antibody.

The use of a monoclonal antibody has the advantage that the antibody is reproducible in standardized fashion, and thus can potentially be produced in unlimited quantities. The binding properties of a monoclonal antibody are furthermore always constant, so that each use of a monoclonal antibody can also be standardized.

In a further preferred embodiment, the antibody used according to the present invention essentially does not interact with immunoglobulins of the IgE class.

The reason is that in studies in conjunction with the activation of basophils, the use of such an antibody offers the unexpected advantage that it does not itself activate the basophils by crosslinking cell-bound IgE immunoglobulins, and thus does not influence the study results.

In a further embodiment of the present invention, antibody 97A6 itself is used for detection and/or isolation.

The use of this antibody has the advantage that this antibody is already well-characterized and is available in large quantities.

The invention further concerns the use according to the present invention of an antibody in conjunction with the analysis of hematopoiesis.

As already mentioned previously, the use according to the present invention creates the possibility of isolating precursor cells of basophils and mast cells, and thus of analyzing hematopoiesis in terms of those cells. This analysis is, however, not only of scientific interest but can also be used in clinical diagnosis in the investigation of blood formation disorders.

In a preferred embodiment, the use according to the present invention of an antibody occurs in conjunction with the analysis of patient samples, in particular of tissue biopsies, bone marrow biopsies, and/or blood samples. In this context, the use according to the invention serves in the case of tissue biopsies to detect mast cells, in the case of bone marrow biopsies to detect precursor cells of mast cells and/or basophils, and in the case of blood samples to detect mature and immature basophils.

As already mentioned, this makes possible, with a single antibody, analyses that differ depending on the starting material and that hitherto could be performed only with antibody combinations or not at all.

The use according to the present invention of an antibody further concerns the diagnostic classification of tumors, in particular of leukemias.

The diagnosis and classification of leukemias is performed on the basis of bone marrow biopsies or blood samples. For example, in one manifestation of leukemia, in CML, the status of all myeloid cells is analyzed based on bone marrow analyses. The antibody according to the present invention has, in this context, the advantage of supplying information about the portion of precursor cells for basophils and mast cells. In a blood analysis, the use according to the present invention makes possible—as already mentioned—the detection of basophils, in particular immature basophils, that hitherto could not be recognized. But since the number of basophils is a critical parameter in the progression of CML, the use according to the present invention offers the advantage of making possible a more reliable diagnostic conclusion than was previously possible as to the stage of the CML.

In a further preferred embodiment of the invention, the antibody used is joined to a marker, in particular to a fluorescent marker.

It is advantageous in this context that the antibody can then be detected with high sensitivity, so that only small quantities of the antibody need to be used for diagnosis. It is also possible to use an antibody of this kind in an ELISA, or when flow cytometry is utilized.

In a further embodiment according to the present invention, the detection of bound antibodies is accomplished by way of a usual immunological detection method, in particular ELISA or FACS analysis.

This use has the advantage that it allows a determination of cells in patient samples that is sensitive, rapid, highly specific, and can be performed in automated fashion.

The invention further concerns the use according to the present invention of an antibody for detecting and/or quantifying activated basophils.

A use of this kind has the advantage of making it relatively easy to investigate the causes of an activation of basophils, since as compared to nonactivated basophils, activated basophils bind a greater number of antibodies used according to the present invention. For example, basophils can be incubated with potentially activating agents and with antibodies used according to the invention. Activated basophils can then be distinguished from nonactivated ones by way of the increased expression of the 97A6 antigen. This enhanced expression can be quantified in the flow cytometer.

The use according to the invention of an antibody moreover concerns the determination of the extent to which basophils are activated.

By determining the extent of antibody binding to individual basophils, it is also possible to determine the extent of antigen expression and thus of the activation of such cells.

This use according to the present invention thus offers the advantageous possibility of investigating agents which activate basophils in terms of the extent to which they contribute to the activation of such cells. Agents, for example allergens, can thus be classified in terms of their ability to activate basophils. It is thereby possible, for example, to estimate the allergy-triggering potential of an agent.

The invention further concerns a method for investigating allergies, comprising the steps:

incubating a blood sample with an agent that is suspected of triggering an allergic reaction;

incubating said blood sample with an antibody used according to the present invention;

quantifying the antibodies bound to cells.

This method according to the present invention creates the possibility of performing an allergy test without having to subject the person being investigated to an annoying and unpleasant skin test. All that is necessary for the method according to the present invention is to perform a test in vitro with various allergens using a few milliliters of blood from the person being tested; 15 minutes after incubation with an agent, incubation can be performed with the antibody used according to the present invention. By quantifying the antibodies bound by the basophils, it is thereby possible to draw a conclusion not only as to whether an agent can trigger an allergic reaction, but also as to the strength of that allergic reaction.

The invention further concerns a method for providing hematopoietic precursor cells that can differentiate into mast cells or basophils, comprising the steps:

isolation and provision of bone marrow cells from an organism;

incubation of said bone marrow cells with an antibody used according to the invention;

isolation of the antibody-bound cells using usual methods, in particular FACS and MACS (magnetically activated cell sorting).

Provision of these hematopoietic precursor cells makes it possible to investigate the development of mast cells and/or basophils. This can be done for research purposes and also, in the case of improper hematopoiesis, for diagnostic purposes. It is also possible to culture from precursor cells, in vitro, cells which later can be introduced back into the donor of the precursor cells without causing immunological problems. This can be useful, for example, in patients exhibiting hematopoietic disorders.

The invention furthermore concerns a substantially pure population of basophils and/or mast cells and/or of the precursor cells of basophils and/or mast cells, said cells being capable of being bound by a reagent that binds specifically to those surface structures of said cells to which antibody 97A6 binds.

Basophils or mast cells do not represent cell lines but rather primary cells, which can only be identified and purified having knowledge of the invention.

The advantage of a population of this kind lies, for example, in the fact that the properties of the cells can thereby be explored very specifically without having the results influenced by other cells. This is important, for example, when the intention is to explore which substances are produced and given off by specific cells under specific conditions, since such substances are generally produced only by a large population of cells in a quantity sufficient that an analysis or identification of said substances can be made therewith. If the population contained different cell types, it would not be possible to draw a conclusion, from the detection of a specific substance, as to which cells were producing that substance.

The invention further concerns a reagent for binding basophils and/or mast cells, and/or the precursor cells of basophils and/or mast cells, that contains an antibody used according to the present invention, preferably antibody 97A6.

The advantage of such a reagent is that cells bound to it can be detected and selected. A further advantage of such a reagent is that it can also contain, in addition to an antibody according to the present invention, further constituents that allow the detection of bound antibodies or the selection of antibody-bound cells. These can be, for example, fluorescent-labeled antibodies or antibodies coupled to magnetic beads, which bind to the antibody according to the present invention.

It is understood that the features mentioned above and those yet to be explained below can be used not only in the respective combinations indicated, but also in other combinations or alone, without leaving the scope of the present invention.

BRIEF DESCRIPTION OF THE DRAWINGS

Further advantages are evident from the following embodiments and in conjunction with the drawings, in which.

DETAILED DESCRIPTION

Example 1

Isolation and detection of basophils from peripheral blood of normal subjects and leukemia patients It is known that the number of basophils in the peripheral blood of patients with CML rises with the transition from the chronic to the accelerated phase.

In order to test the specificity of antibody 97A6 for basophils, mononuclear leukocytes were separated, using Ficoll Hypaque, from other constituents of Buffy Coats from the peripheral blood of normal subjects or patients with CML in the acceleration phase. The interphase cells were then incubated with biotin-labeled antibody 97A6, washed three times, and incubated with anti-IgG MACSbeads (Miltenyi, Bergisch Gladbach, Germany). 97A6-positive cells were then isolated by MACS and then, for preparation monitoring purposes, labeled with phycoerythrin-labeled (PE-labeled) streptavidin and a PE-labeled 97A6 antibody, and analyzed in a flow cytometer.

The purity of the 97A6-positive cells was 99%.

For morphological analysis, these cells were stained with May-Grünwald-Giesma. The result for normal subjects was, in morphological terms as well, a pure basophil population, while only 60 to 80% of the 97A6-positive cells from CML patients in the acceleration phase were morphologically identifiable as basophils. The remaining, morphologically unidentifiable 97A6-positive cells proved to be immature precursor cells of basophils.

This shows that it is possible to recognize a greater portion of the basophils with antibody 97A6 than with the staining method used hitherto.

Example 2

Detection of Tissue Mast Cells Using Antibody 97A6

Lung, foreskin, or uterine tissue was minced, washed in a buffer with 200 mg/l KCl, 50 mg/l $NaH_2PO_4 \times H_2O$, 8 g/l NaCl, and 1 g/l glucose, and then incubated for 90 to 180 minutes at 37° C. with 2 mg/ml collagenase type II (Sebak, Suben, Austria). The dispersed cells were then centrifuged, washed, and incubated for 30 minutes with human AB serum. After being washed again, the cells were incubated for 30 minutes at 4° C. with antibody 97A6, washed, and then incubated for 30 minutes at 4° C. with a fluorescein-labeled goat $F(ab')_2$ IgG anti-mouse antibody. The cells were fixed for 1 minute in 0.025% glutaraldehyde, washed, and incubated for 8–12 minutes with 0.0125% toluidine blue. After washing, toluidine blue-stained mast cells were identified by their morphology using a fluorescence microscope (Olympus, Vienna, Austria) in brightfield mode, and then examined by fluorescent light.

It was found that only mast cells from all the tissues, but not other tissue cells, had been labeled with antibody 97A6. In addition, mast cells exhibited much less fluorescent staining than basophils stained in the same fashion.

Example 3

Isolation and Cultivation of Precursor Cells

Cells from bone marrow samples were centrifuged on Ficoll Hypaque that had a density of 1.077 $g/cm^3$. The interphase cells were isolated, and cells that were positive for CD34 (a marker for hematopoietic precursor cells) were isolated using MACS. These cells were incubated with a FITC-labeled antibody against CD34 and with PE-labeled antibody 97A6. Doubly positive cells were selected by FACS and seeded in a semi-solid ready-made medium containing 0.9% methyl cellulose and a mixture of growth factors including IL-3 (a differentiation factor for basophils and eosinophils) (CellSystems, Remagen, Germany).

After incubation for 16 days at 37° C. in a humidified atmosphere (5% $CO_2$), the resulting colonies were counted, transferred with a Pasteur pipette onto microscope slides, and stained with May-Grünwald-Giesma for morphological examination. In addition to the predominating pure basophil colonies, this examination also revealed mixed eosinophil-basophil, basophil-macrophage, and multipotent basophil-eosinophil-macrophage and/or neutrophil colonies.

This shows that 97A6-positive precursor cells are precursor cells of various myeloid cells, including basophils, that are either limited to the development, bipotent or multipotent.

Example 4

97A6 Antigen Expression During Basophil Development

IL-3 is a stimulator for the growth and differentiation of basophils and their precursor cells. In order to generate basophils from precursor cells, CD34-positive cells were isolated from peripheral blood by MACS, cultivated in serum-free IMDM medium with 700 µg/ml holotransferrin, 40 µg/ml human low-molecular-weight proteins, and 10 µg/ml insulin (Sigma, Munich, Germany), and stimulated with 100 ng/ml IL-3 (Behring-Werke, Marburg, Germany) for 0, 3, 5, 7, 10, and 14 days. To analyze the expression of the 97A6 antigen, the cells were then labeled by means of antibody 97A6 in the manner described in Example 1. The portion of 97A6-positive cells was determined by flow cytometry.

Figure 1:
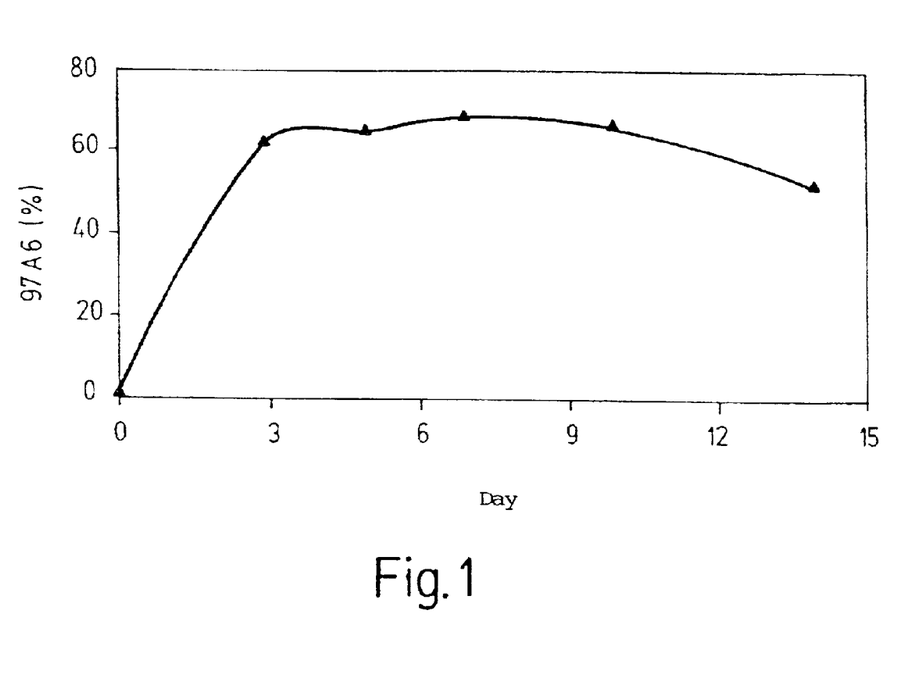
FIG. 1 shows a diagram which depicts the percentage proportion of 97A6-positive CD34$^+$-cells from peripheral blood that were cultivated for 0, 3, 5, 7, 10, and 14 days in vitro in the presence of 100 ng/ml IL-3.

A significant rise was seen in the portion of 97A6-positive cells, from 1±0.5% on day zero of cultivation to more than 60% on the third day of cultivation. This proportion then remained approximately constant, and declined slightly only toward the end of the 14-day cultivation period (FIG. 1).

The morphological evaluation of the 97A6-positive cells after May-Grünwald-Giesma staining revealed predominantly basophils. The rapid rise in the portion of 97A6-positive cells shows that the 97A6 antigen is already being expressed at early stages of basophil development. This is also demonstrated by the experiment described in Example 3, in which precursor cells of basophils were isolated using the 97A6 antigen. This result was also confirmed in Example 1, by the fact that 97A6-positive cells could be identified, as immature basophilic precursor cells, in the peripheral blood of patients with CML in the accelerated phase.

Example 5

Immunoprecipitation of Cell Surface Molecules With Antibody 97A6

Cells of the basophilic precursor cell line KU-812 were surface-labeled with $^{125}I$ and subsequently lysed with NP-40. The immunoprecipitation was performed with pre-assembled 97A6 antibody-complexes. 97A6 antibodies were immobilized on SEPHAROSE beads (a bead form of agarose) that were conjugated with secondary antibodies. As a control, immunoprecipitation was performed with beads without 97A6 antibody After boiling the samples in SDS under reducing conditions in the presence of 2-mercaptoethanol and under non-reducing conditions apparent molecular weights were determined by gel electrophoretical separation on 5–15% polyacrylamide gels (Laemmli, UK, Nature 227 (1970), 680) using $^{14}$C-methylated marker proteins after autoradiography.

Figure 2:
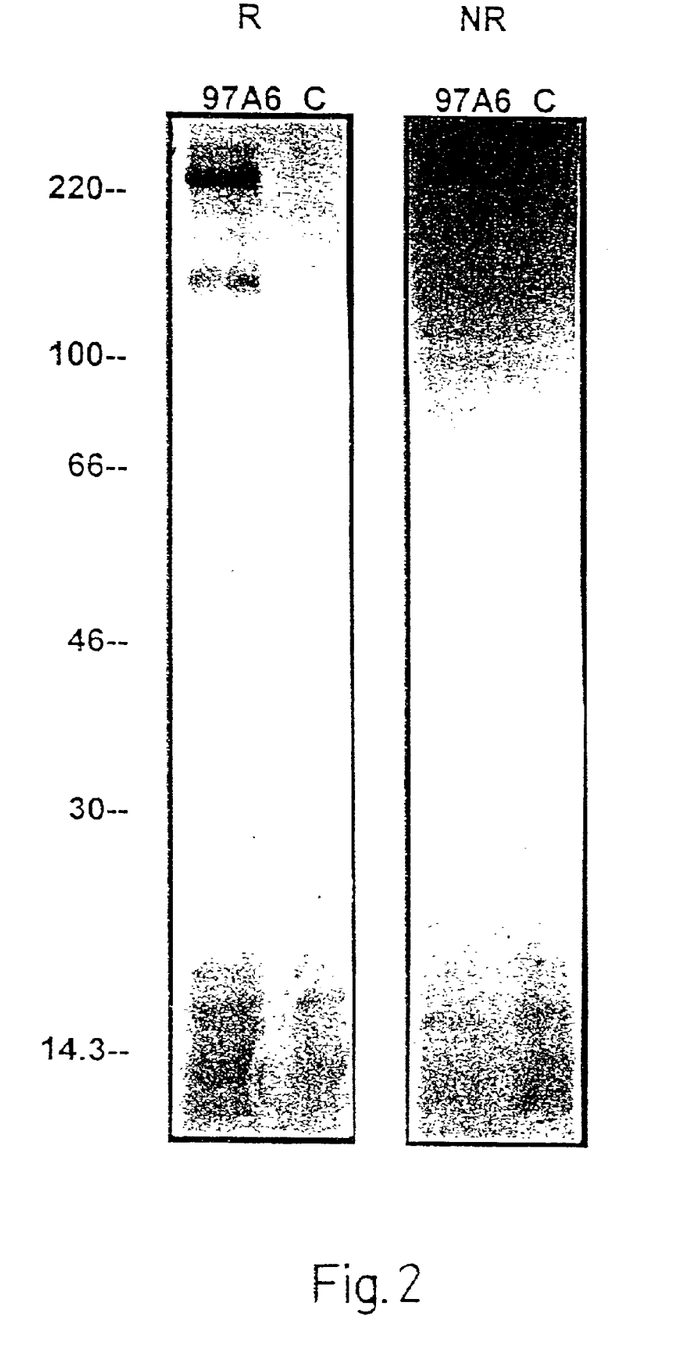
FIG. 2 shows an immunoprecipitation of $10^7$ $^{125}$I surface-labeled and subsequently lysed KU-812 cells with antibody 97A6 (lane 97A6) and a control precipitation without antibody 97A6 (lane C) that were electrophoretically separated on a 5–15% SDS polyacrylamide gel under reducing (R) and non-reducing (NR) conditions and visualized by autoradiography; molecular weight standards are indicated at the left.

The result of this immunoprecipitation is shown in FIG. 2. Proteins with apparent molecular weights of about 270 kD and about 150 kD can be precipitated with antibody 97A6 under reducing conditions and of about 270 kD under non-reducing conditions. The protein complex is a hitherto unknown surface structure that occurs on basophils, mast cells, and their precursor cells.

To identify the molecular structure of the detected antigen KU-812 lysates were purified on a 97A6 antibody column. The eluted protein was separated via SDS-PAGE and the resulting bands were submitted to commercial amino acid sequencing. Comparison with a data bank revealed 100 per cent identity with the recently cloned PDNP3/NPP3 phosphodiesterase/nucleotide pyrophosphatase ectoenzyme.

Example 6

Coexpression of CD Antigens on 97A6-positive Cells

Bone marrow cells (BM), peripheral blood cells (PB), cells from the peripheral blood of CML patients (PB CML), and CD34-positive peripheral blood cells that had been stimulated with 100 ng/ml IL-3 and harvested after three days (d3 PB (+IL-3)) and 14 days (d14 PB (+IL-3)), were stained with 97A6-PE, FITC-conjugated antibodies of the indicated specificity, and with anti-CD34-PerCP antibodies (HPCA-2-PerCP) (Becton Dickinson, Heidelberg, Germany). The FITC-conjugated antibodies against CD10 (W8E7), CD26 (L272), CD44 (L178), CD71 (L01.1), and HLA-DR (L243) (Becton Dickinson), CD13 (SJ1D1), CD16 (3G8), CD33 (D3HL60.251), CD38 (T16) (Immunotech, Krefeld, Germany), CD117 (9B9) (Hölzel Diagnostics, Cologne, German), IgE (polyclonal) (BioSource, Ratingen, Germany), CD55 (1A10) and CD59 (P282H19) (PharMingen, Hamburg, Germany), CD123 (7G3) (PharMingen), CD164 (103B2/9E10) (Zannettino A.C.B. et al., Blood 92 (1998), 2613), CD81 (JS-64) (Immunotech), and CDw17 (MEM74) (BioSource) were respectively incubated together with the cells, the 97A6-PE antibody, and anti-CD34-PerCP for 30 minutes on ice, washed twice, and analyzed using a flow cytometer. The results are presented in Table 1. "+/−" indicate positive subpopulations, and "n.d." means that the corresponding antigen was not detected.

TABLE 1

Coexpression of CD antigens on 97A6-positive cells

| | PB CD34− | PB CD34+ | BM CD34− | BM CD34+ | PB CML | d3 PB (+IL-3) | d14 PB (+IL-3) |
|---|---|---|---|---|---|---|---|
| CD10 | − | n.d. | − | − | − | n.d. | − |
| CD13 | + | − | +/− | +/− | +/− | − | +/− |
| CD16 | − | n.d. | n.d. | n.d. | +/− | n.d. | − |
| CD17 | + | − | +/− | +/− | +/− | +/− | − |
| CD26 | + | − | + | +/− | + | +/− | +/− |
| CD33 | +/− | + | + | + | + | + | |
| CD38 | + | + | + | + | + | + | +/− |
| CD44 | + | + | + | + | + | + | +/− |
| CD55 | + | + | + | + | + | + | + |
| CD59 | + | + | + | + | + | + | + |
| CD71 | − | + | +/− | + | − | + | +/− |
| CD81 | +/− | n.d. | + | + | + | + | + |
| CD117 | − | + | − | + | − | + | n.d. |
| CD123 | + | + | + | + | + | n.d. | |
| CE164 | + | + | + | + | + | − | +/− |
| a-IgE | + | +/− | + | + | − | − | +/− |
| HLA-DR | − | +/− | +/− | + | − | + | +/− |

This study shows that mature basophils (CD34-negative) of peripheral blood are negative for CD117 (a marker for mast cells) and negative for CD71 (a marker for proliferating cells), but express CD17 and a high density of the IL-3 receptor alpha chain (CD123) (a marker for basophils, eosinophils, and monocytes). CD34-negative bone marrow cells appear to express CD13, CD17, CD71, and HLA-DR more heterogeneously than basophils from peripheral blood. A similar expression is seen on basophils from the peripheral blood of CML patients in the acceleration phase. In contrast to the corresponding bone marrow cells, all CD34$^+$97A6$^+$ basophil precursors from peripheral blood are negative for CD13, CD17, and CD26. This shows that the precursors from peripheral blood are somewhat more immature. Both precursors, however, are positive for CD117 and CD71, which do not occur on mature basophils. In contrast to mature basophils from peripheral blood, cultivated 97A6$^+$ basophils obtained from CD34-positive peripheral blood cells by stimulation with IL-3 express little or no CD38, but a high density of HLA-DR molecules.

These data show that the 97A6 antigen is continuously expressed at all stages of basophil maturation, while the expression of CD antigens on basophils at different stages of maturity and from different sources fluctuates markedly.

Example 7

Detection of the Activation of Basophils by Antibody 97A6

Figure 3A:
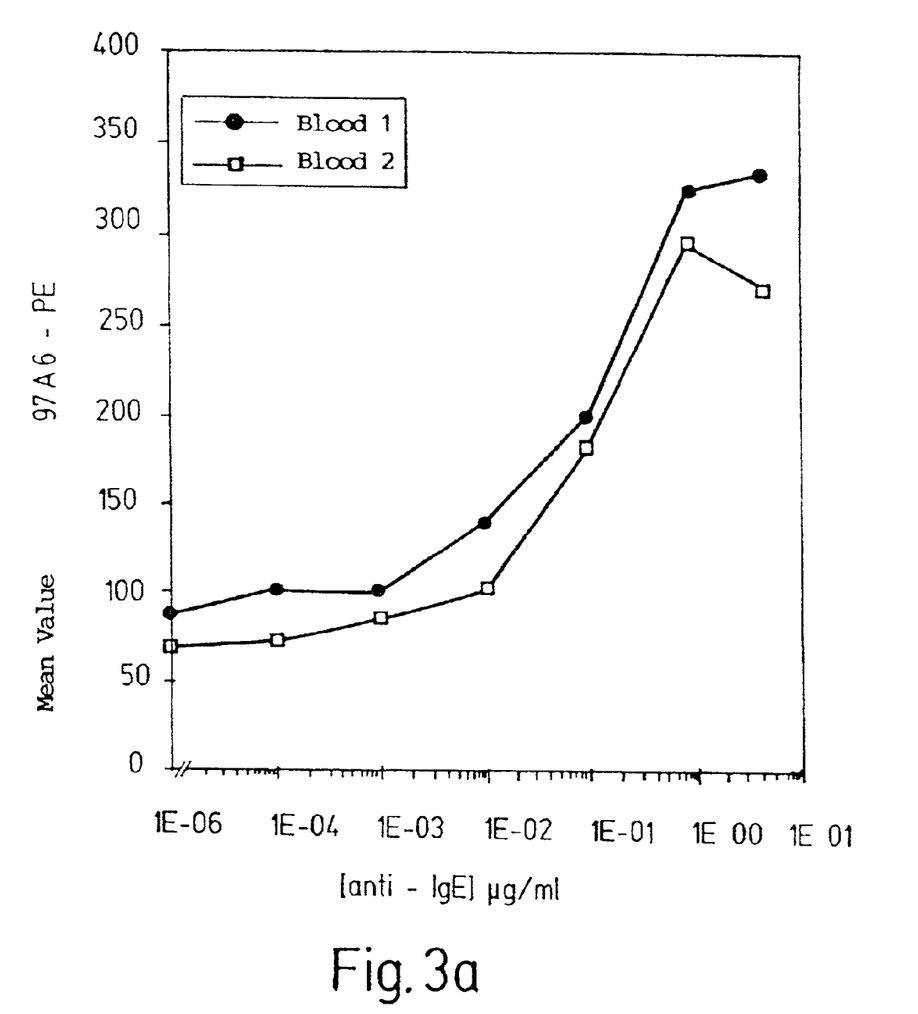
FIG. 3a shows a diagram which depicts the mean quantity of phycoerythrin-labeled antibody 97A6 (97A6-PE) that has bound to basophils, in arbitrary fluorescence intensity units (mean 97A6-PE), the basophils having previously been incubated with the anti-IgE antibody concentrations indicated in the diagram and being derived from the blood of a donor who is allergic to acarids (blood 1) or from the blood of a donor who is not allergic (blood 2)
Figure 3B:
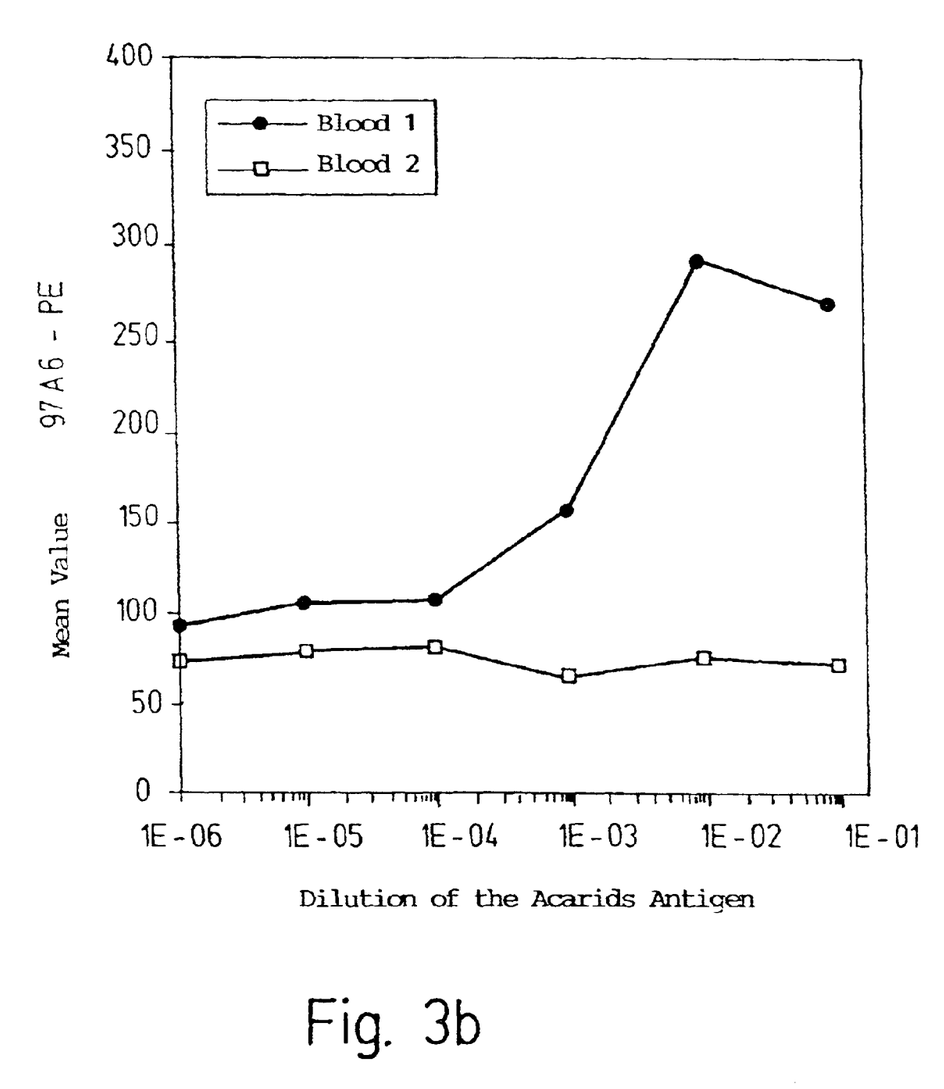
FIG. 3b shows a diagram depicting the mean quantity of 97A6-PE that has bound to basophils, in arbitrary fluorescence intensity units (mean 97A6-PE), the basophils having previously been incubated with the dilutions indicated in the diagram of the acarids antigen, and deriving from the blood of a donor who is allergic to acarids (blood 1) or from the blood of a donor who is not allergic (blood 2).

In this study, depicted in FIGS. 3a and 3b, a blood sample taken from a donor who is allergic to acarids (blood 1) and a blood sample from a donor who is not allergic (blood 2) were each treated with heparin to inhibit coagulation. 100 μl of blood from each sample was then respectively incubated either with an anti-IgE antibody (clone E124-2-8/Dε2, mouse IgG 1, Immunotech) in the final concentrations indicated in FIG. 3a, or with acarids antigens (Stallergenes, Anthony, France) in the dilutions indicated in FIG. 3b, for 15 minutes at 37° C. After each sample had been washed with PBS/20 mM EDTA and the cells had been centrifuged, the cell pellets were resuspended in 100 μl PBS/BSA. 20 μl of antibody 97A6-PE, at a concentration of 25 μg/ml, was added to each sample. After incubation for 15 minutes at room temperature in the dark, the cells were washed and the red blood cells were lysed using IOTest Lysing Reagent (Immunotech no. 486). Following another wash and resuspension of the cells in PBS/BSA, fluorescence was measured in a flow cytometer.

The fluorescent staining at the lowest concentrations of the activators anti-IgE and acarids antigen corresponded to the fluorescent staining without such activators.

The result depicted in FIG. 3a shows that the activation mechanism known for basophils—in which IgE that is bound on the cell surface of basophils is crosslinked by antibodies—results, in the context of activation, in a very rapid presentation of that surface structure on the basophils which is recognized by antibody 97A6.

The result depicted in FIG. 3b shows that only those basophils derived from the donor who is allergic to acarids react to incubation with acarids antigens with an enhanced presentation of the surface structure that is recognized by antibody 97A6. The basophils from the blood of the nonallergic donor, on the other hand, do not exhibit any enhanced presentation of that surface structure following incubation with the acarids antigen.

The underlying mechanism most probably is the fact that the IgE immunoglobulins bound on the basophils of the allergic donor can recognize the acarids antigen and are crosslinked by incubation with that antigen, so that activation of the basophils occurs and the basophils then, as in the case of activation by anti-IgE antibodies, react with an enhanced presentation of the surface structure that is recognized by antibody 97A6. The absence of a reaction in the basophils of the nonallergic donor furthermore shows that antibody 97A6 itself does not result in any activation of the basophils via IgE binding.

It is noteworthy in this context that this presentation requires only 15 minutes of incubation of the cells at 37° C. with the antigen or the anti-IgE antibody.

This test method creates the possibility of performing, with a few milliliters of blood sample, an allergy test in which a wide variety of allergens can quickly be tested to determine whether they can activate the donor's basophils.

What is claimed is:

1. A method for binding cells, comprising:
   providing said cells;
   contacting said cells with antibody 97A6, which is produced by e hybridoma on deposit as No. DSM ACC 2297, to produce a cell-antibody complex;
   separating the cell-antibody complex from unbound cells and/or unbound antibody; and
   detecting a level of the cell-antibody complex,
   wherein said cells are selected from the group consisting of basophils, and mast cells.

2. The method of claim 1, comprising the further step of quantifying said cell-antibody complex.

3. The method of claim 1, further comprising the step of determining the extent to which basophils are activated.

4. The method of claim 1, wherein the antibody is joined to a marker.

5. The method of claim 4, wherein the antibody is joined to a fluorescent marker.

6. The method of claim 1, wherein detection of cell-antibody complex is accomplished by ELISA or FACS analysis.

7. The method of claim 1, further comprising the step of detecting activated basophils.

8. The method of claim 7, further comprising the step of determining the extent to which basophils are activated.

9. The method of claim 1, wherein said cells are provided as a patient sample, wherein said patient sample is selected am the group consisting of tissue biopsies, bone marrow biopsies, and blood samples.

* * * * *

UNITED STATES PATENT AND TRADEMARK OFFICE
CERTIFICATE OF CORRECTION

PATENT NO. : 6,949,346 B2
DATED : September 27, 2005
INVENTOR(S) : Buhring et al.

It is certified that error appears in the above-identified patent and that said Letters Patent is hereby corrected as shown below:

Title page,
Item [57], ABSTRACT,
Line 1, "for the detection quantification" should read -- for the detection, quantification --.

Column 12,
Lines 6-7, "produced by e hybridoma" should read -- produced by the hybridoma --.
Line 31, "am the group" should read -- from the group --.

Signed and Sealed this

Twenty-fourth Day of January, 2006

JON W. DUDAS
*Director of the United States Patent and Trademark Office*